United States Patent
Rebolledo Berríos

(10) Patent No.: US 12,290,647 B2
(45) Date of Patent: May 6, 2025

(54) PUNCTURE DEVICE FOR ACCESSING THE VASCULAR SYSTEM

(71) Applicant: South 53 LLC, San Juan Capistrano, CA (US)

(72) Inventor: Hernán Rebolledo Berríos, Punta Arenas (CL)

(73) Assignee: South 53 LLC, San Juan Capistrano, CA (US)

( * ) Notice: Subject to any disclaimer, the term of this patent is extended or adjusted under 35 U.S.C. 154(b) by 882 days.

(21) Appl. No.: 17/259,441

(22) PCT Filed: Jul. 12, 2018

(86) PCT No.: PCT/CL2018/050055
§ 371 (c)(1),
(2) Date: Jan. 11, 2021

(87) PCT Pub. No.: WO2020/010478
PCT Pub. Date: Jan. 16, 2020

(65) Prior Publication Data
US 2021/0275781 A1   Sep. 9, 2021

(51) Int. Cl.
*A61M 25/06* (2006.01)
*A61M 25/00* (2006.01)

(52) U.S. Cl.
CPC ........ *A61M 25/06* (2013.01); *A61M 25/0023* (2013.01); *A61M 2025/0008* (2013.01);
(Continued)

(58) Field of Classification Search
CPC .............. A61M 25/06; A61M 25/0023; A61M 2025/0008; A61M 2025/0024;
(Continued)

(56) References Cited

U.S. PATENT DOCUMENTS

| 3,515,137 A | 6/1970 | Santomieri |
| 4,642,101 A | 2/1987 | Krolikowski et al. |

(Continued)

OTHER PUBLICATIONS

International Search Report and Written Opinion for related International Application No. PCT/CL2018/50055, mailed on Jan. 2, 2019; English translation of ISR provided; 9 pages.

(Continued)

*Primary Examiner* — Nathan R Price
*Assistant Examiner* — Haden Matthew Ritchie
(74) *Attorney, Agent, or Firm* — Pillsbury Winthrop Shaw Pittman, LLP

(57) ABSTRACT

The present invention is related to the field of devices for introducing and extracting media from the body, more specifically to the devices for introducing media into the body by means of intravascular access, and in particular, provides a puncture device for accessing the vascular system comprised of: a needle having a tubular body, with said tubular body having a distal end and a proximal end, a cutting edge in the distal end of said tubular body, and an expansion of the external diameter having a bulb shape next, in distal-proximal direction, to said cutting edge.

In this way, a puncture device is provided for accessing the vascular system that solves the problem of allowing the echograph monitoring of the needle, but whose fabrication implies a reduction in the technical difficulty for its obtention, while it avoids the accidental perforation of the distal wall of the vessel of interest.

18 Claims, 3 Drawing Sheets

(52) U.S. Cl.
CPC ............. *A61M 2025/0024* (2013.01); *A61M 2025/0042* (2013.01)

(58) Field of Classification Search
CPC .... A61M 2025/0042; A61M 2205/583; A61M 5/158; A61B 17/0218
See application file for complete search history.

(56) References Cited

U.S. PATENT DOCUMENTS

| | | | |
|---|---|---|---|
| 6,433,929 B1 | 8/2002 | Sasaki et al. | |
| 8,439,892 B2* | 5/2013 | Hoofnagle | A61M 25/0074 604/524 |
| 9,066,690 B2 | 6/2015 | Steube | |
| 9,566,087 B2 | 2/2017 | Bierman et al. | |
| 9,700,697 B2 | 7/2017 | Gasparyan et al. | |
| 2010/0106092 A1 | 4/2010 | Tanabe et al. | |
| 2012/0265229 A1* | 10/2012 | Rottenberg | A61M 25/0084 606/170 |
| 2013/0110049 A1* | 5/2013 | Cronenberg | A61M 5/3157 604/239 |
| 2014/0343456 A1* | 11/2014 | Cabot | A61B 5/150236 600/581 |
| 2015/0342635 A1* | 12/2015 | Tsamir | A61B 17/3476 604/164.04 |
| 2017/0095314 A1* | 4/2017 | Baldwin | A61M 25/09 |
| 2017/0296798 A1* | 10/2017 | Kume | A61M 39/24 |
| 2018/0133442 A1* | 5/2018 | Adriaens | A61M 25/0108 |
| 2020/0345989 A1* | 11/2020 | Do | B29C 49/04 |

OTHER PUBLICATIONS

International Search Report mailed Jan. 2, 2019 in International Patent Application No. PCT/CL2018/050055 (2pgs.).

* cited by examiner

PUNCTURE DEVICE FOR ACCESSING THE VASCULAR SYSTEM

CROSS-REFERENCE TO RELATED APPLICATIONS

This application is a U.S. National Stage entry of PCT Application No: PCT/CL2018/050055 filed Jul. 12, 2018, the contents of which are incorporated herein by reference.

TECHNICAL FIELD OF THE INVENTION

The present invention is related to the field of devices for introducing and extracting media from the body, more specifically to devices for introducing media into the body by means of intravascular access, and particularly provides a puncture device for accessing the vascular system.

BACKGROUND OF THE INVENTION

In the field of the puncture techniques for vascular access, a significant difficulty is the maintenance of the quality of the echographic visualization of the tip of the needles used for said puncture. During the procedure, the loss of the visual continuity of the cutting edge of the needle being used could lead the operator to produce an unnoticed perforation of the distal wall of the vascular structure being punctured, therefore damaging the structures near the vessel being punctured.

Some solutions in the prior art are the use of puncture needles having a modified external surface in which troughs or notches are uniformly and periodically distributed along their lengths. In this way, the ultrasound waves are partially reflected by these structures, which allows monitoring said needle.

Other solutions are related to the presence of visual tests for verifying the puncture of the vessel of interest. For example, document U.S. Pat. No. 9,700,697 describes, as part of the prior art, a catheter comprising a flexible portion and a needle which is inserted in said flexible portion. The proximal end of said needle is in fluid communication with a reservoir that serves as a visual test for verifying the puncture of the vessel of interest, by means of the presence of blood into the same reservoir. Document U.S. Pat. No. 9,066,690, on the other hand, describes a needle for blood extraction comprising a deposit having a base portion and an extension. This extension defines a transparent or translucid duct. Additionally, two cannulas are included, one of them being configured for perforating the vessel, whereas the second one is in fluid communication with an adequate reservoir that acts as visual test for verifying the puncture.

Nevertheless, the needles of the prior art which have a modified external surface have a high cost due to the technical difficulty of providing a needle having troughs or notches along its surface. On the other hand, the devices which include a needle in fluid communication with an indicator do not necessarily solve the problem of the loss of echographic vision.

On the other hand, it is accepted that a great portion of the injuries caused by the intention of accessing the inside of a vessel are the consequence of the inadvertent puncture of adjacent structures. This fact is not removed, even when ultrasound monitoring techniques are used for guiding the puncture needle or trocar, because there is an impossibility of stopping the advance puncture tool after the vessel has been punctured.

In the prior art, there do not exist needles that allow stopping the advance of the puncture while, at the same time, define a supporting point over the wall of the vessel or other body structures in order to completely avoid the inadvertent advance of the puncture tool beyond the desired point.

Consequently, it is required a puncture device for accessing the vascular system that solves the problem of allowing the monitoring of the needle by means of echograph vision, but whose manufacture implies a reduction in the technical difficulty for its obtention.

SUMMARY OF THE INVENTION

The present invention provides a puncture device for accessing the vascular system which comprises: a needle having a tubular body, said tubular body having a distal end and a proximal end; a cutting edge in the distal end of said tubular body; and an expansion of the external diameter having a bulb shape next, in distal-proximal direction, of the said cutting edge.

In a preferred embodiment, the puncture device is characterized in that said tubular body has a single bulb shaped expansion of the external diameter next to said cutting edge.

In another preferred embodiment, the puncture device is characterized in that said bulb shaped expansion of the external diameter has a fusiform shape.

In an additional preferred embodiment, the puncture device is characterized in that said tubular body has a visible mark along its length that coincides with the back of said cutting edge, as an extension of the longest portion of said cutting edge, said visible mark extending substantially parallel to the axis of said tubular body. In a further preferred embodiment, said visible mark is a trough or etching on the external surface of said tubular body.

In another preferred embodiment, the puncture device additionally comprises a mandrel inserted into said tubular body, wherein said mandrel has an elongated piece having a distal end and a proximal end, said elongated piece having a canal along its length; and a reservoir, positioned next in a distal-proximal direction to the proximal end of said elongated piece, said reservoir being in fluid communication with said canal. In a further preferred embodiment, the puncture device is characterized in that said elongated piece of the mandrel has a length that corresponds to the length of the tubular body of the needle. In an even further preferred embodiment, said puncture device is characterized in that the distal end of the elongated piece of the mandrel has an edge that coincides with the cutting edge of the tubular body of the needle.

In a further preferred embodiment, the device is characterized in that said reservoir has a window in optical communication with the inside of said reservoir. In an even further preferred embodiment, said reservoir comprises a plurality of windows, each window being in optical communication with the inside of the reservoir. In another further preferred embodiment, the device is characterized in that said reservoir has a cylindrical shape having a portion of its surface in optical communication with its inside.

In another further preferred embodiment, said tubular body of said needle and said elongated piece of said mandrel have a shape that allows the insertion of said mandrel into the tubular body in a single position.

In another further preferred embodiment, the puncture device is characterized in that said needle has a first connector in the proximal end of the said tubular body and the mandrel has a second connector in the proximal end of the elongated body, said second connector being complementary to said first connector. In an even further preferred embodiment, said first connector and said second connector have a shape that allows the insertion of the mandrel into the tubular body in a single position. In another even further preferred embodiment, said first connector and said second connector are luer lock type connectors.

DETAILED DESCRIPTION OF THE INVENTION

Following, the invention will be described in detail, making reference to the figures that accompany the present application.

Figure 1:
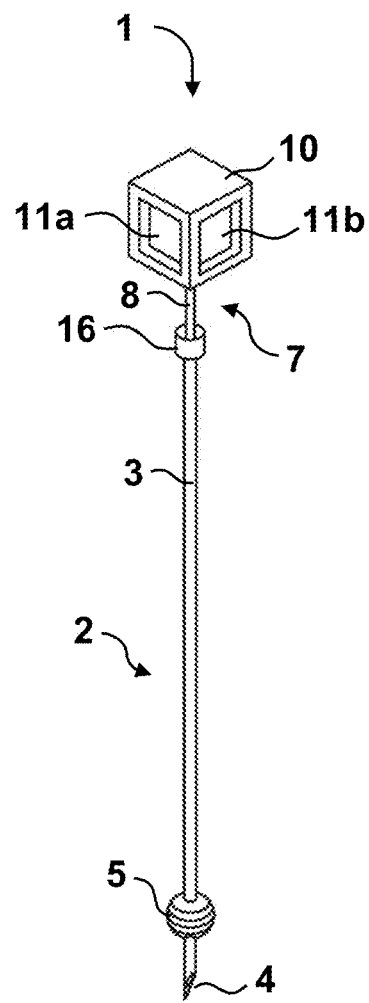
FIG. 1 shows an isometric view of a first embodiment of the puncture device of the present invention.
Figure 2:
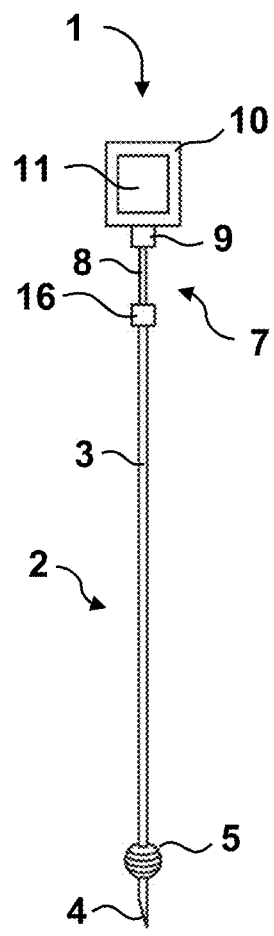
FIG. 2 shows a front view of a first embodiment of the puncture device of the present invention.

As shown in FIGS. 1 and 2, the present invention provides a puncture device (1) for accessing the vascular system, essentially comprising: a needle (2) comprising a tubular body (3), said tubular body (3) having a distal end and a proximal end, a cutting edge (4) in the distal end of said tubular body (3), and an expansion of the external diameter (5) having a bulb shape next, in a distal-proximal direction, to said cutting edge (4).

In the context of the present invention, it is to be understood that the terms "distal" and "proximal" are referred to a specialist performing the puncture for accessing the vascular system of a patient which may be human or animal. In this sense, the distal portion of an object or element is the farthest portion from said specialist, whereas the proximal portion of said object or element is the closest portion to said specialist.

On the other hand, it is to be understood as "vascular system" the set of ducts in the body of said patient, through which the blood may circulate and which includes arteries, veins, arterioles, venules, and capillaries.

Additionally, when a bulb shape is referred to, it is to be understood that such a shape is substantially obtained by the revolution around an axis of a curved surface and includes, without being limited to these, fusiform shapes, spheroids, ellipsoids, ovoids, spheres, and others.

Regarding the tubular body (3) of the needle (2) that is part of the puncture device (1) being object of the present invention, the length and diameter, both internal and external, of the same do not limit the scope of the present invention. Generally, without limiting the scope of the present invention and as is known by a person ordinarily skilled in the relevant art, the ratio between the length and the diameter, both internal and external, of said tubular body are related to the diameter of the structure to be punctured and to the deepness at which said structure is from the body surface. Said length may be, for example and without limiting the scope of the invention, in the range from 15 mm to 150 mm, whereas the external diameter may be between 1.5 mm and 3 mm and the internal diameter between 1 mm and 2.5 mm. In the same way, the length of the cutting edge (4) located at the distal end of said tubular body (3) does not limit the scope of the present invention. A way for obtaining said cutting edge (4), without limiting the scope of the invention, is by means of a cut at an angle of less than 90° with respect to the axis of the tubular body (3). In said case, the value of said angle does not limit the scope of the present invention and is, preferably, in the range from 5° to 35°.

Regarding the expansion of the external diameter (5) having a bulb shape, the same fulfills three duties. On one hand, said expansion of the external diameter (5) having a bulb shape enhances the echogenicity of the needle (2) that is part of the puncture device (1) of the present invention. The previous is due to the ultrasound waves interacting in a different way with said expansion of the external diameter (5) than with the rest of the tubular body (3) of the said needle (2). On the other hand, said expansion of the external diameter (5) having a bulb shape, operates as a resting point of said needle (2) on the external proximal wall of the vessel to be punctured. In this way, the perforation of the distal wall of said vessel is avoided because said expansion of the external diameter (5) having a bulb shape stops the progression of the said needle (2) in a proximal-distal direction, which may also be visually verified by the specialist by means of a notable deformation of the proximal wall of the vessel, which is visible by echographic monitoring. Once the proximal wall has been punctured, this resting point also allows the axis of the needle to be rotated without further difficulties, allowing the back of the needle to contact the inside of the vessel. This maneuver makes the axis of the needle to converge with the axis of the vessel, facilitating the safe introduction of guides into the vessel. Finally, and without limiting the scope of the invention, said expansion of the external diameter (5) having a bulb shape may allow to dilate the path of the needle (2) of the puncture device (1) of the present invention, which may allow the subsequent introduction of other devices, such as an endovascular catheter by means of the Seldinger technique.

Figure 3:
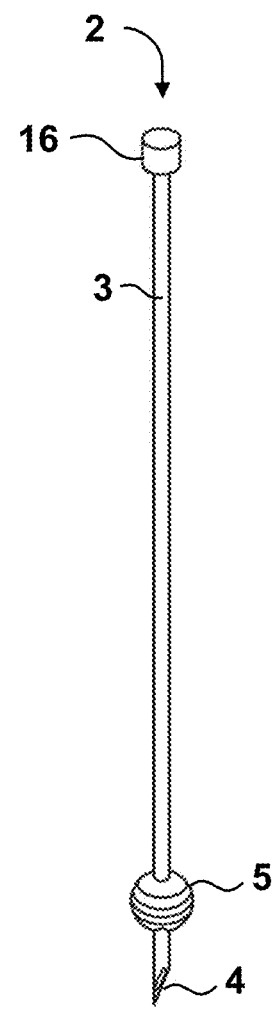
FIG. 3 shows an isometric view of a first embodiment of the needle that is part of the puncture device of the present invention.
Figure 4:
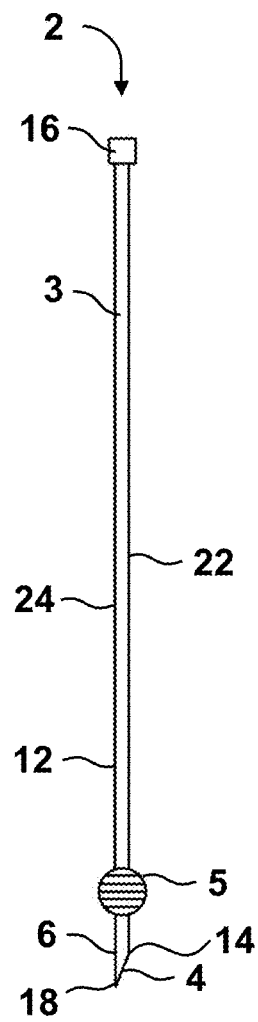
FIG. 4 shows a front view of a first embodiment of the needle that is part of the puncture device of the present invention.

A first preferred embodiment of the said needle (2) is shown in FIGS. 3 and 4. In said preferred embodiment, without limiting the scope of the present invention, the needle (2) which is part of the puncture device (1) of the present invention, has a single expansion of the external diameter (5) having a bulb shape next, in a distal-proximal direction, to the cutting edge (4). In the context of the present invention, without limiting the scope of the same, it is to be understood that said expansion of the external diameter (5) having a bulb shape is positioned next to said cutting edge (4) when the distance between the proximal end (14) of said cutting edge (4) at a first side (22) of the needle (2) and the distal end of said expansion of the external diameter (5) having a bulb shape is between O mm and 5 mm, preferably between O mm and 2 mm, and more preferably, when said distance is lower than 1 mm. On the other hand, the specific dimensions of said expansion of the external diameter (5) having a bulb shape do not limit the scope of the present invention. For example, and without limiting the scope of the present invention, the greatest external diameter of said expansion of the external diameter (5) may be between 0.5 mm and 1.5 mm larger than the external diameter of the tubular body (3). On the other hand, the longitudinal extension of said expansion of the external diameter (5) having a bulb shape does not limit the scope of the present invention and may be, for example, and without limiting the scope of the present invention, between 3 mm and 10 mm. A person ordinarily skilled in the relevant art will note that the ratios between the diameter of the tubular body (3) of said needle (2), the total length of said tubular body (3), the dimensions of said expansion of the external diameter (5) and the distance separating said expansion of the external diameter (5) and the cutting edge (4) of said tubular body will depend, without limiting the scope of the present invention, on the diameter, the deepness and the thickness of the wall of the vessel to be punctured.

Nevertheless, in case that said needle (2) of the puncture device (1) of the present invention includes more than one expansion of the external diameter (5) having a bulb shape, each of them may be obtained according to the previous description without limiting the scope of the present invention. In this case, the expansions of the external diameter (5) may be equal or different without limiting the scope of the invention, and may be placed at equal distances between them, or at unequal distances without limiting the scope of the present invention.

On the other hand, optionally and without limiting the scope of the invention, said needle (2) may include a visible mark (12) along the length of said tubular body (3), wherein said visible mark coincides with the back of said cutting edge (6) and extends essentially parallel to the axis of said tubular body (3). In this sense, it is to be understood that the back of said cutting edge (6) is aligned with the most distal end (18) of said cutting edge (4) and, therefore, it is the portion that coincides with the longest length of the tubular body (3) on a second side (24) of the needle (2), opposite the first side (22) of the needle (2) which is part of the puncture device (1) which is the subject of the present invention. In this manner, said visible mark extends coinciding with the longest portion of the tubular body (3) of the needle (2). Said visible mark fulfills the function of helping the specialist to identify the longest portion for allowing an adequate access to the vessel of interest. Additionally, once the proximal wall of said vessel has been punctured, said visible mark also allows the rotation of said tubular body (3) of the needle (2) using as a resting point the expansion of the external diameter (5). In this way, it is further allowed to contact the inside of the vessel with the back of said tubular body (3) of the needle (2). This maneuver allows the axis of the vessel to be substantially parallel to the axis of the tubular body (3) of the needle (2), facilitating, in this way, the introduction of guides into the vessel. In a preferred embodiment, without limiting the scope of the invention, said visible mark is a trough or a notch that extends along the external surface of the tubular body (3).

In another optional embodiment, without limiting the scope of the invention, said needle (2) has a handle (not shown in the figures) in the proximal portion of said tubular body (3). In this sense, it is to be understood that a handle is any surface, projection or coupling, as well as a combination thereof, that facilitates the manipulation of said needle by the specialist. Said handle may facilitate both the introduction and the rotation of the needle (2) of the puncture device (1) of the present invention.

Optionally, as is shown in FIGS. 1 and 2 and without limiting the scope of the invention, the puncture device (1) of the present invention additionally comprises a mandrel (7) that may be inserted into said tubular body (3) of said needle (2). Said mandrel (7) has an elongated piece (8) having a distal end and a proximal end, said elongated piece (8) also having a canal (not shown in the figures) along its length; and a reservoir (10), positioned next, in distal-proximal direction, to the proximal end of said elongated piece (8), with said reservoir (10) being in fluid communication with said canal.

Figure 5:
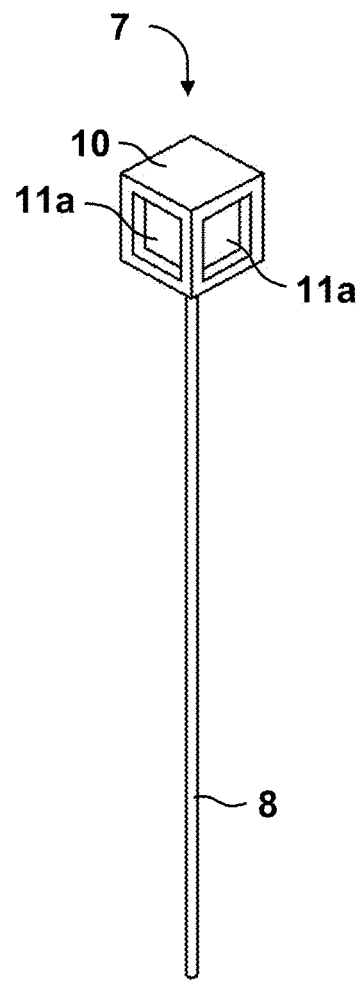
FIG. 5 shows an isometric view of a first embodiment of the mandrel that is part of the puncture device of the present invention.
Figure 6:
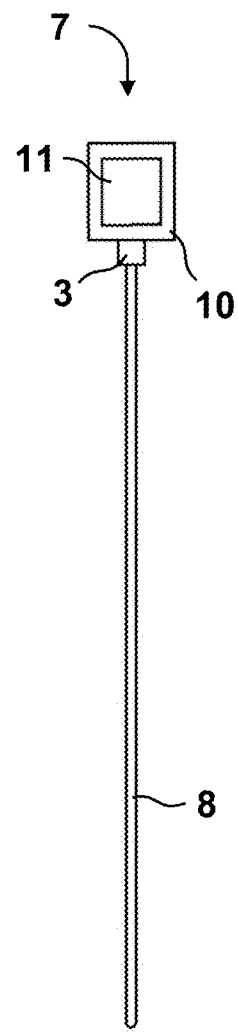
FIG. 6 shows a front view of a first embodiment of the mandrel that is part of the puncture device of the present invention.
Figure 7:
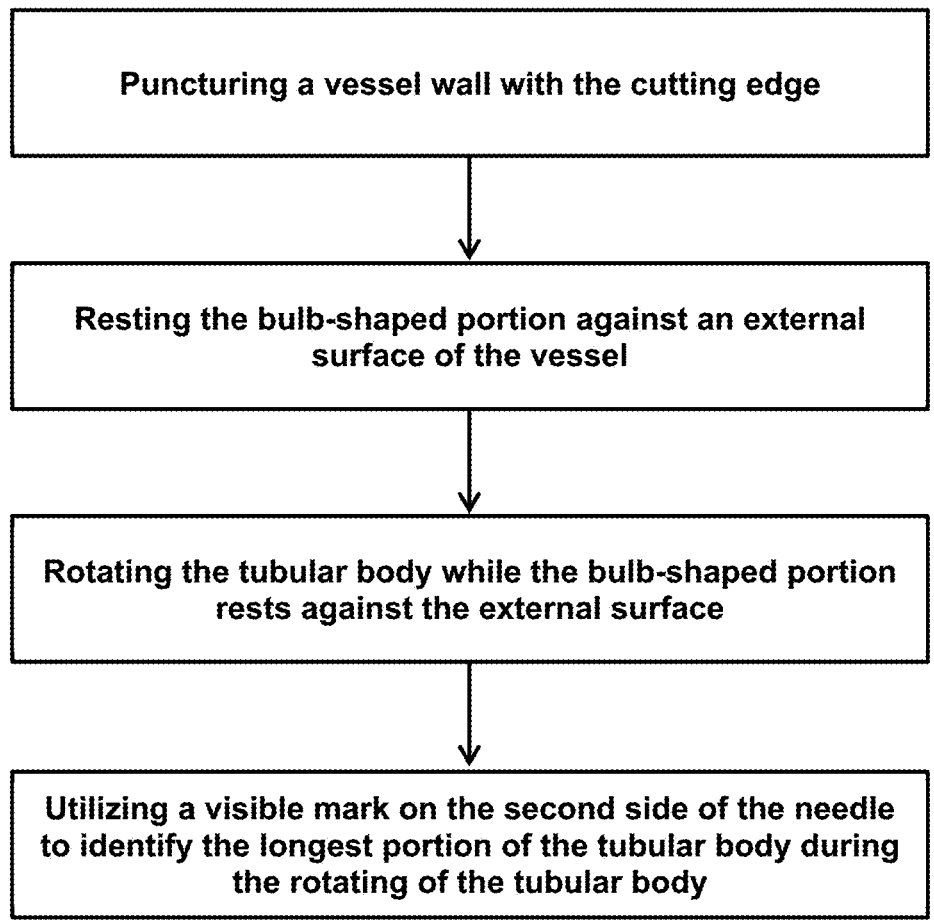
FIG. 7 is directed to the method of the present application.

A preferred embodiment of said mandrel (7) is shown in FIGS. 5 and 6. Said mandrel (7) fulfills the function of temporarily occluding the lumen of the needle (2) while said needle (2) is being introduced into its target, in this way avoiding the introduction of soft tissue into the needle (2) and, consequently, its obstruction. This also decreases the pain due to the introduction of the needle (2) through the soft tissues of the body surface. Finally, a greater mechanical stability is achieved in the needle (2) which is part of the puncture device (1) of the present invention. Consequently, the elongated piece (8) of said mandrel (7) must possess a portion whose lateral dimensions are smaller than the internal diameter of the tubular body (3) of said needle (2). On the other hand, the canal being present in said elongated piece (8) may be a surface canal, having the shape of a trough, or an internal canal, having the shape of a longitudinal perforation, without limiting the scope of the present invention. In the case in which said canal is an internal canal, said elongated piece (8) is configured as a second tubular body. Additionally, the dimensions of said elongated piece (8) are such that they allow to fulfill the functions previously detailed. For example, and without limiting the scope of the present invention, in a preferred embodiment, said elongated piece (8) has a length that corresponds to the length of the tubular body (3) of said needle (2). In a further preferred embodiment, additionally and without limiting the scope of the present invention, the distal end of the elongated piece (8) of said mandrel (7) has an edge (not shown in the figures) that corresponds to the cutting edge (4) of the tubular body (3) of the needle (2), in such a way that the distal end of said elongated piece (8) is configured as a continuation of the distal end of the tubular body (3). This shape allows the mandrel (7) to protect the inside of said tubular body (3) of the needle (2) from the distal end of said tubular body (3).

In another preferred embodiment, and without limiting the scope of the present invention, said tubular body (3) of said needle (2) and said elongated piece (8) of said mandrel (7) may have a shape that allows the insertion of said mandrel (7) into said tubular body (3) in a single position. For example, and without limiting the scope of the present invention, said relation is obtained when the internal cross section of said tubular body (3) and the external cross section of said elongated piece (8) have a shape that does not allow the rotation between them. This allows that, in use, said needle (2) and said mandrel (7) act as a single body, minimizing the difficulty of their use. Additionally, without limiting the scope of the present invention, said configuration allows the profile of the mandrel (7) to coincide with the tubular body (3) of the needle (2).

Additionally, the reservoir (10) positioned next to the proximal end of said elongated piece (8) fulfills the function of being a visual test of the perforation of the vessel of interest. The fluid communication between the canal and said reservoir (10) allows the blood to flow through said canal into said reservoir (10), which is filled with blood once the vessel of interest is perforated. In the context of the present invention, it is to be understood that the reservoir (10) is next to the proximal end of the elongated piece (8) when said reservoir (10) is in a further proximal position than said proximal end. Therefore, the distance between said proximal end and said reservoir (10) does not limit the scope of the present invention. On the other hand, the specific shape and dimensions of said reservoir (10) do not limit the scope of the present invention.

In a preferred embodiment, without limiting the scope of the present invention, said reservoir (10) comprises a window (11) in optical communication with the inside of said reservoir (10). In such a way, it is possible to see the inside of said reservoir (10) from the outside and to visually verify the puncture of the vessel of interest. In a further preferred embodiment, without limiting the scope of the present invention, said reservoir (10) comprises a plurality of windows (11a, 11b), wherein each of said windows (11a, 11b) is in optical communication with the inside of said reservoir (10). This last configuration has the advantage of making it possible to verify the puncture of the vessel of interest regardless of the alignment of the line of sight of the specialist with said reservoir (10). In another preferred embodiment, without limiting the scope of the present invention, said reservoir (10) is a transparent vial. In another preferred embodiment, said reservoir (10) has a cylindrical shape, and may be fully transparent or present a portion of its surface in optical communication with its inside.

In a preferred embodiment, and in order to provide an appropriate coupling between the needle (2) and the mandrel (7) which are part of the puncture device (1) of the present invention, corresponding connectors may be provided in said needle (2) and said mandrel (7) without limiting the scope of the present invention. For example, and without limiting the scope of the present invention, said needle (2) may have a first connector (16) in the proximal end of the tubular body (3), whereas said mandrel (7) may have a second connector (9), complementary to said first connector (16) in the proximal end of the elongated piece (8). Any type of previously known connector in the prior art may be used without limiting the scope of the present invention. Additionally, said connectors (16, 9) may allow a single use or multiple uses without limiting the scope of the present invention. For example, and without limiting the scope of the present invention, said first connector 16 and said second connector (9) may be of the luer lock type, which are broadly known and used in the prior art.

In another preferred embodiment, without limiting the scope of the present invention, said first connector (16) and said second connector (9) have a shape that allows the insertion of said mandrel (7) in a single position into the tubular body (3) of said needle (2). Said preferred embodiment is obtained when, once they are coupled, said mandrel (7) and said needle (2) cannot rotate between themselves. For example, and without limiting the scope of the present invention, said first connector (16) may have a notch and said second connector (9) may have a projection with a complementary shape to said notch. This allows that, during use, said mandrel (7) and said needle (2) will behave as a single body, minimizing the difficulty in their use. Additionally, and without limiting the scope of the present invention, when said mandrel (7) has a cutting edge, this configuration allows the bezel of said mandrel (7) to coincide with the cutting edge (4) of the tubular body (3) of the needle (2).

According to the previously detailed description, it is possible to obtain a puncture device (1) for accessing the vascular system that possess a series of advantages with respect to the devices previously known in the prior art.

In the first place, an optimal echographic visualization is obtained, because the difference of diameters between the expansion of the external diameter (5) having a bulb shape and the rest of the tubular body (3) generates an echographic distortion that notoriously improves the visualization of the cutting edge (4) in the distal end. Additionally, said expansion of the external diameter (5) having a bulb shape offers a greater contact surface with the wall of the vessel of interest, which produces a notable deformation of the perimeter of the vessel (when seen in cross section) making it to adopt a shape like a coffee bean, which further improves the tactile perception of the wall by the operator.

On the other hand, a stable resting point is created in the wall of the vessel, because the expansion of the external diameter (5) having a bulb shape curtails the advance of the needle (2). Thus, the operator is allowed to keep a hand in the echograph transducer, while he or she may perform a rotation of the tubular body (3) of the 5 needle (2) to allow an adequate access, avoiding the risk of perforating the distal wall of the vessel.

Additionally, said expansion of the external diameter (5) allows to arrange the needle (2) in a way that is more parallel to the axis of the vessel to be punctured, which facilitates the insertion of guides or other elements, through the inside of said needle (2) into the vessel.

In this way, it is provided a puncture device (1) for accessing the vascular system that solves the problem of allowing the echograph monitoring of the needle, but whose manufacture implies a reduction in the technical difficulty for its obtention, while it avoids the accidental perforation of the distal wall of the vessel of interest.

The invention claimed is:

1. A puncture device for accessing a vessel within the vascular system, comprising:
    a needle with a tubular body, the needle having an angled cutting edge at a distal end of the tubular body for puncturing the vessel within the vascular system, the tubular body having an external diameter;
    the angled cutting edge extending distally from a proximal end of the angled cutting edge at a first side of the needle to a distal end of the angled cutting edge at a second side of the needle opposite the first side, the tubular body having an outer surface with its longest longitudinal length extending along the second side of the needle and terminating at the distal end of the angled cutting edge, wherein the angled cutting edge forms an acute angle with respect to the outer surface of the needle along the second side of the needle;
    the puncture device including an echogenic bulb-shaped portion having an external diameter greater than the external diameter of the tubular body, the echogenic bulb-shaped portion having greater echogenicity relative to the tubular body, a distal end of the bulb-shaped portion providing a stop configured to rest against and deform an exterior surface of the vessel that has been punctured by the cutting edge while permitting rotation of the needle while the bulb-shaped portions rest against the exterior surface, the bulb-shaped portion curtailing further progress of the cutting edge into the vessel; and
    a visible mark on the outer surface along the second side of the needle and extending parallel to a longitudinal axis of the tubular body to enable a user to identify the longest portion of the tubular body when accessing a vessel within the vascular system.

2. The puncture device of claim 1, wherein the bulb-shaped portion has a fusiform shape.

3. The puncture device of claim 1, wherein the bulb-shaped portion has a proximal end and a distal end, and wherein a distance between a proximal end of the cutting edge and a distal end of the bulb-shaped portion is between 0 mm to 5 mm.

4. The puncture device of claim 1, wherein the bulb-shaped portion has a proximal end and a distal end, and wherein a distance between a proximal end of the cutting edge and a distal end of the bulb-shaped portion is between 0 mm to 2 mm.

5. The puncture device of claim 1, wherein the external diameter of the bulb-shaped portion is greater than the external diameter of the tubular body by an amount between 0.5 mm and 1.5 mm.

6. The puncture device of claim 3, wherein the external diameter of the bulb-shaped portion is greater than the external diameter of the tubular body by an amount between 0.5 mm and 1.5 mm.

7. The puncture device of claim 1, wherein the visible mark is a trough or etching on an external surface of the tubular body.

8. The puncture device of claim 1, wherein the bulb-shaped portion is configured to facilitate rotation of the puncture device while the bulb-shaped portion rests against the exterior surface of the vessel.

9. The puncture device of claim 1, wherein the cutting edge comprises a bevel, and wherein the visible mark is formed on an exterior surface of the tubular body opposite the bevel.

10. The puncture device of claim 1, wherein the cutting edge has a proximal end and a distal end, wherein the bulb-shaped portion has a proximal end and a distal end, and wherein a distance between a proximal and of the cutting edge and a distal end of the bulb-shaped portion is less than 1 mm.

11. A method for a user accessing the vascular system with a puncture device, the puncture device comprising:
   a needle with a tubular body, the needle having an angled cutting edge at a distal end of the tubular body for puncturing the vessel within the vascular system, the tubular body having an external diameter;
   the angled cutting edge extending distally from a proximal end of the angled cutting edge at a first side of the needle to a distal end of the angled cutting edge at a second side of the needle opposite the first side, the tubular body having an outer surface with its longest length extending along the second side of the needle and terminating at the distal end of the angled cutting edge, wherein the angled cutting edge forms an acute angle with respect to the outer surface of the needle along the second side of the needle;
   the puncture device including an echogenic bulb-shaped portion having an external diameter greater than the external diameter of the tubular body, the echogenic bulb-shaped portion having greater echogenicity relative to the tubular body, a distal end of the bulb-shaped portion configured to rest against an exterior surface of the vessel that has been punctured by the cutting edge, and the method comprising:
   puncturing a vessel wall with the cutting edge;
   resting the bulb-shaped portion against an external surface of the vessel, the bulb shaped portion providing a stop that curtails penetration of the cutting edge into the vessel wall;
   rotating the tubular body while the bulb-shaped portion rests against the external surface; and
   utilizing a visible mark on the second side of the needle to identify the longest portion of the tubular body during the rotating of the tubular body.

12. The method of claim 11, further comprising contacting a proximal wall of the punctured vessel with the outer surface of tubular body on the second side of the needle, such that a longitudinal axis of the tubular body is substantially parallel to a longitudinal axis of the vessel.

13. The method according to claim 11, further comprising maneuvering the needle such that a longitudinal axis of the needle converges towards a longitudinal axis of the vessel.

14. The method according to claim 11, wherein contact between the bulb-shaped portion and the vessel wall causes a deformation in the vessel wall.

15. A puncture device for accessing a vessel within the vascular system, comprising:
   a needle with a tubular body, the needle having an angled cutting edge for penetrating the vessel at a distal end of the tubular body for puncturing the vessel within the vascular system, the angled cutting edge being at an acute angle with respect to a longitudinal axis of the tubular body, the tubular body having an external diameter;
   the puncture device including an echogenic bulb-shaped portion having an external diameter greater than the external diameter of the tubular body, the echogenic bulb-shaped portion having an echogenicity greater than an echogenicity of the tubular body, a distal end of the bulb-shaped portion configured to rest against and deform an exterior surface of the vessel that has been punctured by the cutting edge while permitting rotation of the needle while the bulb-shaped portion rests against the external surface of the vessel, and
   wherein the bulb-shaped portion has a proximal end, and wherein a distance between a proximal end of the cutting edge and a distal end of the bulb-shaped portion is between 0 mm to 5 mm, the distal end of the echogenic bulb-shaped portion providing a stop surface to limit penetration of the cutting edge to said distance.

16. The puncture device of claim 15, wherein the distance between the proximal end of the cutting edge and the distal end of the bulb-shaped portion is between 0 mm to 2 mm.

17. The puncture device of claim 15, wherein the bulb-shaped portion has a fusiform shape.

18. The puncture device of claim 15, wherein the angled cutting edge extends distally from a proximal end of the angled cutting edge at a first side of the needle to a distal end of the angled cutting edge at a second side of the needle opposite the first side, wherein the distal end of the angled cutting edge is disposed at a longest portion of the tubular body, and further comprising a visible mark on the second side of the needle to enable a user to identify the longest portion of the tubular body when accessing a vessel within the vascular system.

* * * * *